(12) United States Patent
Feng et al.

(10) Patent No.: US 10,196,344 B2
(45) Date of Patent: Feb. 5, 2019

(54) GLAUCOCALYXIN A DERIVATIVE AND PREPARATION METHOD AND APPLICATION THEREOF

(71) Applicant: SUZHOU PHARMAVAN CANCER RESEARCH CENTER CO., LTD., Jiangsu (CN)

(72) Inventors: Haimei Feng, Jiangsu (CN); Rensen Zhou, Jiangsu (CN); Xiang Chen, Jiangsu (CN); Yunhui Yu, Jiangsu (CN); Qian Liu, Jiangsu (CN); Yong Li, Jiangsu (CN); Shiping Deng, Jiangsu (CN); Chuangliang Jiang, Jiangsu (CN)

(73) Assignee: SUZHOU PHARMAVAN CANCER RESEARCH CENTER CO., LTD., Jiangsu (CN)

( * ) Notice: Subject to any disclaimer, the term of this patent is extended or adjusted under 35 U.S.C. 154(b) by 0 days.

(21) Appl. No.: 15/561,685

(22) PCT Filed: Dec. 17, 2015

(86) PCT No.: PCT/CN2015/097692
§ 371 (c)(1),
(2) Date: Sep. 26, 2017

(87) PCT Pub. No.: WO2016/150207
PCT Pub. Date: Sep. 29, 2016

(65) Prior Publication Data
US 2018/0079711 A1    Mar. 22, 2018

(30) Foreign Application Priority Data

Mar. 26, 2015 (CN) ............ 2015 1 0138028
Mar. 26, 2015 (CN) ............ 2015 1 0138029
May 13, 2015 (CN) ............ 2015 1 0243692

(51) Int. Cl.
| A61P 35/00 | (2006.01) |
| A61P 37/00 | (2006.01) |
| C07C 221/00 | (2006.01) |
| C07C 225/12 | (2006.01) |
| C07D 207/00 | (2006.01) |
| C07D 233/60 | (2006.01) |
| C07D 473/18 | (2006.01) |
| C07D 295/116 | (2006.01) |

(52) U.S. Cl.
CPC ............ *C07C 225/12* (2013.01); *A61P 35/00* (2018.01); *A61P 37/00* (2018.01); *C07C 221/00* (2013.01); *C07D 207/00* (2013.01); *C07D 233/60* (2013.01); *C07D 295/116* (2013.01); *C07D 473/18* (2013.01); *C07C 2603/86* (2017.05)

(58) Field of Classification Search
CPC ........ A61P 35/00; A61P 37/00; C07C 221/00; C07C 225/12; C07C 237/30; C07C 2603/86; C07D 207/00; C07D 233/60; C07D 295/116; C07D 473/18
See application file for complete search history.

(56) References Cited

FOREIGN PATENT DOCUMENTS

| CN | 101851273 A | 10/2010 |
| CN | 101914002 A | 12/2010 |
| CN | 101993370 A | 3/2011 |
| CN | 103601641 A | 2/2014 |
| CN | 104761460 A | 7/2015 |
| CN | 104817464 A | 8/2015 |
| CN | 104887652 A | 9/2015 |

OTHER PUBLICATIONS

Yang et al., "Synthesis and biological evaluation of glaucocalyxin A derivatives as potential anticancer agents," European Journal of Medicinal Chemistry, 86 (2014) 235-241 (Year: 2014).*
Hoelder et al., "Discovery of small molecule cancer drugs: Successes, challenges and opportunities," Molecular Oncology 6 (2012) 155-176. (Year: 2012).*
Yang, Jing et al. "Synthesis and biological evaluation of glaucocalyxin A derivatives as potential anticancer agents", European Journal of Medicinal Chemistry, 86: 235-241 (2014).
International Search Report, dated Mar. 22, 2016, in corresponding International Application No. PCT/CN2015/097692.
International Search Report, dated Mar. 23, 2016, in corresponding International Application No. PCT/CN2015/097693.
International Search Report, dated Apr. 1, 2016, in corresponding International Application No. PCT/CN2015/097691.

* cited by examiner

*Primary Examiner* — Pancham Bakshi
*Assistant Examiner* — Mark R Luderer
(74) *Attorney, Agent, or Firm* — Robert C. Netter, Jr.; Dann, Dorfman, Herrell & Skillman

(57) ABSTRACT

Provided is a glaucocalyxin A derivative, or salt thereof, as represented by the formula (I), a method for preparation of said glaucocalyxin A derivative, and a use for said glaucocalyxin A derivative in preparing pharmaceuticals for fighting autoimmune diseases and tumors, e.g. difficult-to-treat diseases such as systemic lupus erythematosus, psoriasis and triple-negative breast cancer

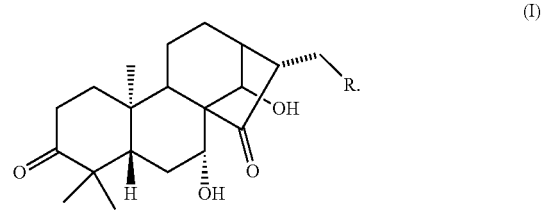

19 Claims, 6 Drawing Sheets

GLAUCOCALYXIN A DERIVATIVE AND PREPARATION METHOD AND APPLICATION THEREOF

CROSS-REFERENCE TO RELATED APPLICATIONS

This application is a § 371 of International Application No. PCT/CN2015/097692, filed Dec. 17, 2015, which claims priority from Chinese Patent Application No. 201510138028.6, filed Mar. 26, 2015, Chinese Patent Application No. 201510138029.0, filed Mar. 26, 2015 and Chinese Patent Application No. 20150243692.7, filed May 13, 2015. The entire disclosure of each of the aforesaid applications is incorporated by reference in the present application.

FIELD OF THE INVENTION

The present invention relates to the field of chemical medicine, particularly relates to glaucocalyxin A derivative and preparation method and application thereof.

BACKGROUND OF THE INVENTION

Glaucocalyxin A (hereinafter referred to as GLA), also known as "wangzaozi ne B", is extracted from the whole part above ground of Rabdosia japonica (Burm.f.) Hara var. glaucocalyx (Maxim.) Hara which belongs to the family labiatae. Glaucocalyxin A has the chemical name of Kaur-16-ene-3,15-dione,(7α, 14R)—, the molecular formula of $C_{20}H_{28}O_4$ and the molecular weight of 332.43, and the structure as shown below:

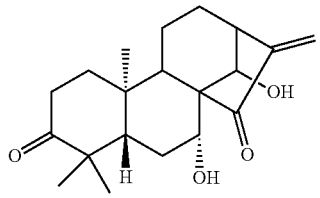 [SMILES: C=C1C(=O)C23C(O)C1CCC2[C@]1(C)CCC(=O)C(C)(C)[C@H]1C[C@H]3O]

The content of glaucocalyxin A in dry leaves of the Rabdosia japonica (Burm.f.) Hara var. glaucocalyx (Maxim.) Hara is up to 1.03% [Yuantong Zhang, Dongxu Sha, Ming Sha et al., China Journal of Chinese Materia Medica, 1991, 16 (11):679]. It has a structure similar to oridonin, and belongs to the ent-Kaurane diterpenoids. In its structure, there is also the anti-tumor group, α,β-unsaturated cyclopentanone structural unit, which is similar to oridonin. In vitro and in vivo anti-tumor experiments have shown that it has a significant inhibitory effect on proliferation of various human tumor cell strains (CE-1, U87, A549, MCF-7, Hela, K562, HepG2, NCI-H460, KB, JEG-3, K562, HL-60), especially for the cells of hormone non-dependent prostate cancer (DU-145) and rectal cancer (Lovo), and has a wide range of anti-tumor effects; it can inhibit the growth of solid tumors such as Lewis lung cancer, S180 solid type and HCA solid type and the like, and significantly increase the life extension rate of S180 ascites type and HCA ascites type mice, and the effect of anti-tumor effect is dose-dependent. The recent literature in 2011 [Li WenGao, Jian Zhang, Wen Hua Yang, Bin Wang, Jian Wen Wang. Toxicology in Vitro 2011, 25: 51-63] has reported that glaucocalyxin A can induce apoptosis through mitochondria-regulated death pathway to inhibit the proliferation of human promyelocytic leukemia cell, and thus it is a promising precursor compound with anti-tumor activity.

In addition, as a drug against autoimmune disease, glaucocalyxin A has made a breakthrough in the treatment of systemic lupus erythematosus and psoriasis and the like, and has achieved good therapeutic effect. It has been pointed out in the literature "Research Progress of Rabdosia amethystoides(Benth)Hare" [Yu Su, Jia Cui, Wuwu Shi et al., The Asia-pacific Traditional Medicine, 2011, June] that glaucocalyxin A obtained from Rabdosia japonica not only has anti-cancer, anti-bacterial, liver protection and cardiovascular protection effects, but also is active in autoimmune suppression.

However, glaucocalyxin A has a low polarity and poor water solubility, and thus is not suitable for direct administration as a drug; it has strong anti-autoimmune and anti-tumor effects in vitro, while in vivo it requires a large dose and a long time to produce efficacy. It is rapidly cleared in vivo and has a short half-life and a low bioavailability in vivo, and cannot be used directly as a drug yet. Therefore, as an effective way to solve its shortcomings as a drug, under the premise of retaining the active group α,β-unsaturated cyclopentanone, an exocylic double bond is structurally modified to synthesize derivative which has stronger anti-autoimmune and anti-tumor effects.

SUMMARY OF THE INVENTION

The glaucocalyxin A derivative and preparation method and application thereof are provided by the present invention, in order to solve the technical problems described above.

Particularly, in a first aspect, the present invention provides a glaucocalyxin A derivative represented by formula (I):

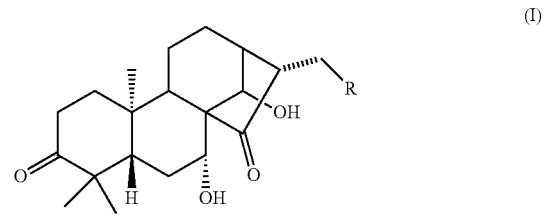

wherein R is any one selected from the group consisting of dimethylamino, diethylamino, piperidine-1-yl, piperazine-1-yl, hexamethyleneiminyl, morpholine-1-yl, N-phenyl-N-(3-oxcocyclohexanyl)amino, N-p-chlorophenyl-N-(2-oxo-butanyl)amino, N-2-chlorophenyl-N-(2-oxo-butanyl)amino, benzylamino, purinyl-9-yl, 2-amino-6-hydroxypurine-9-yl, 4-methylpiperazine-1-yl, N-phenyl-N-m,ethyl-amino, dibenzyl-amino, imidazole-1-yl, 2-methyl imidazole-1-yl, N-phyenyl-N-(3-oxo-butanyl)amino, pyrrole-1-yl, 2-hydroxyacylpyrrole-1-yl, 2-methylpyrrolidine-1-yl, 3-methylpyrrole-1-yl, 2-oxo-pyrrole-1-yl, 3-aminoacylphenylamino, p-aminoacylphenylamino, amino acid substitional;

or salt thereof.

The glaucocalyxin A derivative provided by the present invention shows high targetability in its anti-autoimmune and anti-tumor effects and can be used as an active compound to further develop novel pharmaceutical formulations for the chemical treatment of autoimmune diseases and the treatment of cancer diseases. In particular, the glaucocalyxin A derivative of the present invention is expected to fill the gaps in the medical treatment of systemic lupus erythematosus, psoriasis and triple-negative breast cancer.

In a preferred embodiment, the R group is a dimethylamino group, and the glaucocalyxin A derivative is dimethylamino glaucocalyxin A hydrochloride, with a structural formula of formula II below:

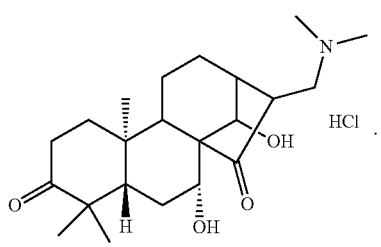

II

The $^1$H NMR spectrum and the $^{13}$C NMR spectrum of the dimethylamino glaucocalyxin A hydrochloride represented by the formula II are shown in FIG. 1 and FIG. 2, respectively, and the LC-MS spectrum thereof is shown in FIG. 3. As can be seen from FIGS. 1 to 3, the dimethylamino glaucocalyxin A hydrochloride has a molecular formula of: $C_{22}H_{36}C_1NO_4 \cdot HCl$.

The inventors have found that, by means of experiments, the dimethylamino glaucocalyxin A hydrochloride represented by the formula II has good water solubility, and has high oral bioavailability when used as a drug. Moreover, it shows high targetability in its anti-autoimmune and antitumor effects and is expected to fill the gaps in the medical treatment of systemic lupus erythematosus, psoriasis and triple-negative breast cancer.

In a second aspect, the present invention provides a method for the preparation of glaucocalyxin A derivative according to the first aspect, which comprises subjecting the glaucocalyxin A and a R group donor compound to an addition reaction in the present of a catalyst to afford the product.

In the above method for the preparation, it is preferable that the catalyst is any one or more selected from the group consisting of sodium methoxide, sodium ethoxide, pyridine, sodium carbonate and potassium carbonate.

Preferably, the mole ratio of the R group to the glaucocalyxin A is (1 to 10): 1;

Preferably, the mole ratio of the catalyst to the glaucocalyxin A is (1 to 10): 1.

Preferably, the reaction is carried out at a temperature between −30 and 60

Preferably, the reaction is carried out in a solvent;

Further preferably, the solvent comprises any one or more selected from the group consisting of alcohol, ketone, ether, ester and haloalkane; more further preferably, the alcohol comprises any one or more selected from the group consisting of methanol, ethanol, isopropanol, isobutanol and tert-butanol; the ketone comprises any one or more selected from the group consisting of acetone and 2-butanone; the ether comprises any one or more selected from the group consisting of ethyl ether, dioxane, isopropyl ether, methyl tert-butyl ether and tetrahydrofuran; the ester comprises any one or more selected from the group consisting of methyl acetate, ethyl acetate and butyl acetate; the haloalkane comprises dichloromethane and trichloromethane;

Further preferably, the method for the preparation further comprises a step of evaporating the solvent and/or detecting with TLC and/or HPLC after the reaction.

In a third aspect, the present invention provides a method for the preparation of the salt of glaucocalyxin A derivative according to the first aspect, comprising:

dissolving the glaucocalyxin A derivative into an organic solvent to form a solution, then subjecting the solution and an acid to a salt formation reaction, while controlling the pH of the solution, to give the salt of glaucocalyxin A derivative.

In the method for the preparation, preferably, the acid includes organic acid and inorganic acid;

Further preferably, the inorganic acid comprises any one selected from the group consisting of hypoiodous acid, hypochlorous acid, hypobromous acid, iodic acid, perchloric acid, peroxydisulfuric acid, peroxydicarbonic acid, peroxycarbonic acid, pyrophosphoric acid, pyrosulfuric acid, pyrosulfurous acid, tetrathioic acid, phosphoric acid, thiosulfuric acid, sulfuric acid, chloric acid, metaphosphoric acid, hydroiodic acid, hydronitric acid, hydrofluoric acid, hydrogen sulfide, hydrochloric acid, hydrobromic acid, tetraboric acid, carbonic acid, nitric acid, bromic acid, sulfurous acid, phosphorous acid, chlorous acid, hydrochloric acid, nitrous acid, orthophosphoric acid, orthosulfuric acid and orthocarbonic acid.

Further preferably, the organic acid comprises any one selected from the group consisting of tartaric acid, oxalic acid, malic acid, citric acid, ascorbic acid, benzoic acid, salicylic acid, caffeic acid, lactic acid, sorbic acid, fumaric acid, formic acid, acetic acid, benzoic acid, ethanedioic acid, succinic acid, pyruvic acid, α-keto-succinic acid, benzenesulfonic acid, ethanesulfonic acid, resin acid, trifluoroacetic acid, maleic acid, tetrasulfonic acid, methanesulfonic acid, fumaric acid and amino acid.

Preferably, the organic solvent comprises any one or more selected from the group consisting of alcohol, ketone, ether, ester and haloalkane;

Further preferably, the alcohol comprises any one or more selected from the group consisting of methanol, ethanol, isopropanol, isobutanol and tert-butanol; the ketone comprises any one or more of the following group consisting of acetone and 2-butanone; the ether comprises any one or more selected from the group consisting of ethyl ether, dioxane, isopropyl ether, methyl tert-butyl ether and tetrahydrofuran; the ester comprises any one or more selected from the group consisting of methyl acetate, ethyl acetate and butyl acetate; the haloalkane comprises dichloromethane and trichloromethane.

Preferably, the pH of the solution is controlled by hydrogen chloride solution;

Further preferably, the hydrogen chloride solution comprises any one selected from the group consisting of aqueous solution of hydrogen chloride, methanol solution of hydrogen chloride, ethanol solution of hydrogen chloride, isopropanol solution of hydrogen chloride, n-propanol solution of hydrogen chloride, isobutanol solution of hydrogen chloride, ethyl acetate solution of hydrogen chloride, acetone solution of hydrogen chloride, ethyl ether solution of hydrogen chloride and dioxane solution of hydrogen chloride.

Preferably, the pH of the solution is controlled between 6.0 and 8.0.

Preferably, the reaction is carried out at a temperature between −30 and 60

In a fourth aspect, the present invention provides the use of glaucocalyxin A derivative or a salt thereof according to the first aspect in the manufacture of a medicament for the treatment of an autoimmune disease and/or the treatment of a cancer;

Preferably, the autoimmune disease is systemic lupus erythematosus or psoriasis;

Preferably, the cancer comprises any one or more selected from the group consisting of triple-negative breast cancer, glioma, cervical cancer, esophageal cancer, lung cancer, liver cancer, choriocarcinoma, oral epidermoid carcinoma, prostate cancer, rectal cancer.

Advantages

Compared with glaucocalyxin A, the glaucocalyxin A derivative provided by the present invention shows high targetability in its anti-autoimmune and antitumor effects and can be used as an active compound to further develop novel pharmaceutical formulations for the chemical treatment of autoimmune diseases and the treatment of cancer diseases. In particular, the glaucocalyxin A derivative of the present invention is expected to fill the gaps in the medical treatment of diseases such as systemic lupus erythematosus, psoriasis and triple-negative breast cancer.

DESCRIPTION OF THE DRAWINGS

The drawings to be used in the description of the examples will be briefly described below, in order to illustrate the technical solutions of the embodiments of the present invention more clearly. Apparently, the drawings in the following description are only embodiments of the invention, and other drawings may be obtained by those skilled in the art without creative work.

DETAILED DESCRIPTION

Figure 1:
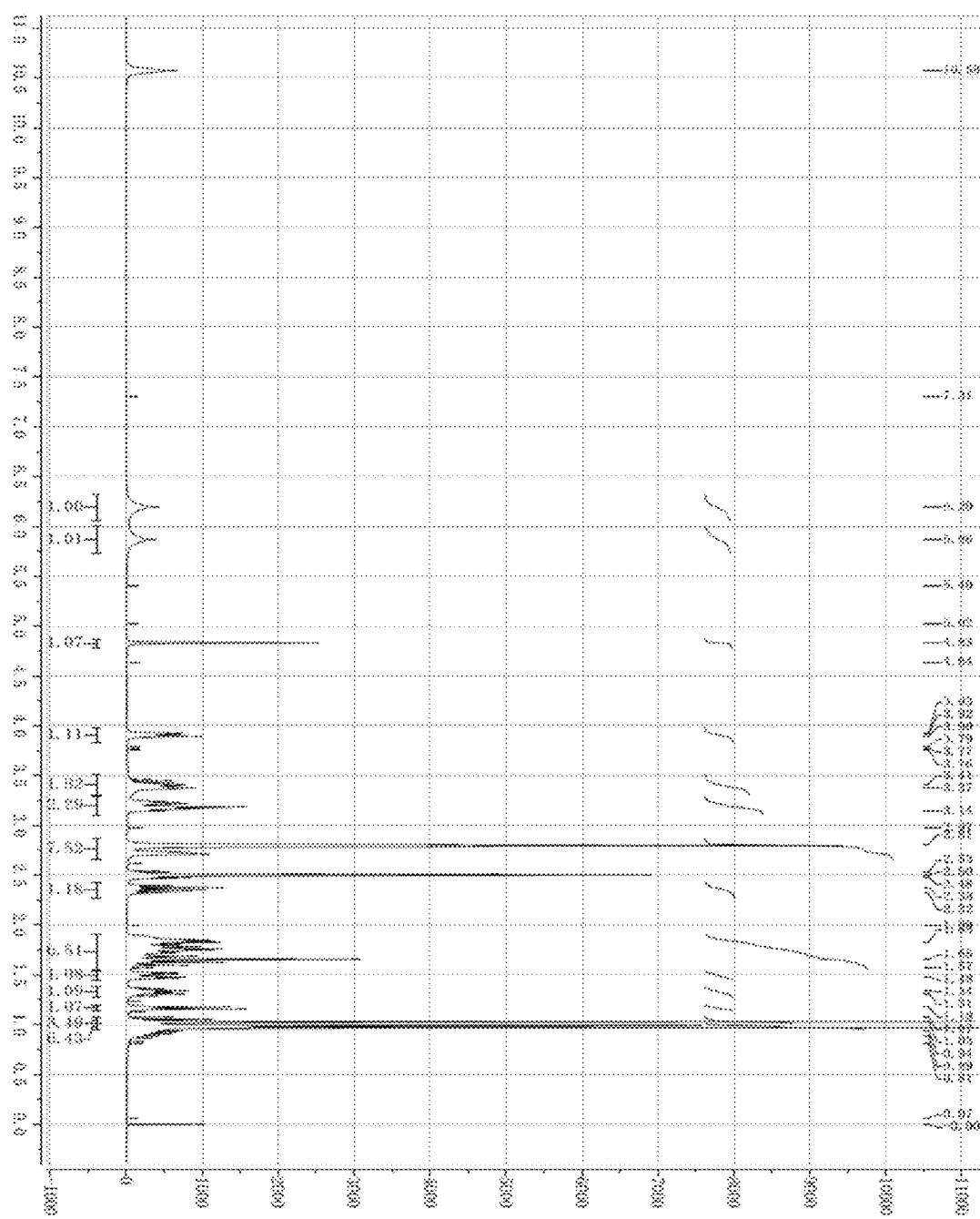
FIG. 1 shows a $^1$H NMR spectrum of a glaucocalyxin A derivative of the present invention.

The technical solutions in the embodiments of the present invention will be described, clearly and completely, with the combination of the drawings in the embodiments of the present invention. Obviously, the described embodiments are only part of the present invention rather than all. All other embodiments obtained by those general skilled in the art under the premise of no creative work, on the basis of embodiments of the present invention, are within the scope of the present invention.

EXAMPLE 1

This example discloses a method for the preparation of a glaucocalyxin A derivative, comprising: glaucocalyxin A nitrogenous derivative which was obtained by modification of glaucocalyxin A, was reacted with an acid to give a salt of glaucocalyxin A nitrogenous derivative with good solubility in water.

Wherein, the modification reaction equation from glaucocalyxin A to glaucocalyxin A nitrogenous derivative is shown as below:

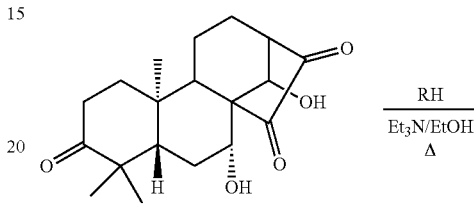

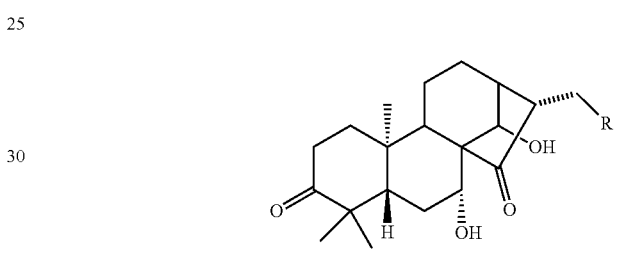

The glaucocalyxin A (GLA) was used as raw material, and the catalyst was used in an amount so that the molar ratio of the catalyst to the raw material glaucocalyxin A was 1 to 10, and the temperature was controlled between −30

The R in RH is a donor of nitrogen, and has a structure identical to that of R in glaucocalyxin A derivative. R is any one of the following groups: dimethylamino, diethylamino, piperidine, piperazine, hexamethyleneimine, morpholine, N-methy 1piperazine, methylaniline, dibenzylamine, imidazole, 2-methyl imidazole, 4-Phenylamino-butanone, 3-(phenyl amino) cyclohexanone, p-chlorophenyl-amino-butanone, o-chlorophenyl-amino-butanone, benzylamine, purine, 2-amino-6-hydroxypurine, Pyrrole, pyrrole-2-carboxylic acid, 2-methylpyrrolidine, 3-methylpyrrole, 3-aminobenzamide, p-aminobenzamide and various amino acid.

The obtained glaucocalyxin A derivative has a structural formula as shown below:

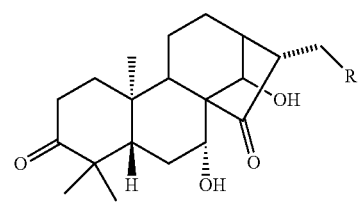

The structure of R in the above structural formula may be any one of the structures of the group in Table 1:

TABLE 1

The name and structure of R group

| Name of the Group | Structure of the Group | Name of the Group | Structure of the Group |
| --- | --- | --- | --- |
| dimethylamino | N(CH₃)₂ | 4-methyl piperazine-1-yl | |
| diethylamino | N(CH₂CH₃)₂ | N-phenyl-N-methyl-amino | |
| piperidine-1-yl | | dibenzylamin0 | |
| Piperazine-1-yl | | Imidazole-1-yl | |
| hexamethyleneiminyl | | 2-methyl imidazole-1-yl | |
| Morpholine-1-yl | | N-phenyl-N-(3-oxo-butanyl)amino | |
| N-phenyl-N-(3-oxocyclohexanyl)amino | | Pyrrole-1-yl | |
| N-p-chlorophenyl-N-(2-oxo-butanyl)amino | | 2-hydroxyacylpyrrole-1-yl | |
| N-2-chlorophenyl-N-(2-oxo-butanyl)amino | | 2-methylpyrrolidine-1-yl | |
| benzylamino | | 3-methylpyrrole-1-yl | |
| purinyl-9-yl | | 2-oxo-pyrrole-1-yl | |

TABLE 1-continued

The name and structure of R group

| Name of the Group | Structure of the Group | Name of the Group | Structure of the Group |
|---|---|---|---|
| 2-amino-6-hydroxypurine-9-yl | (structure: guanine-like bicyclic ring with HN, C=O, $H_2N$, and imidazole N atoms) | 3-aminoacylphenyl amino | $H_2NOC$—(phenyl, meta)—NH |
| amino acid substitutional | —COOH attached to $NH_2$ | p-aminoacylphenyl amino | $H_2NOC$—(phenyl, para)—NH |

The glaucocalyxin A derivative described as above was then reacted with an acid to give a salt of glaucocalyxin A derivative with good solubility in water. The acid which can react with glaucocalyxin A derivative includes those shown in Table 2.

TABLE 2

The acids which can react with glaucocalyxin A derivative

| Inorganic Acid | | Organic Acid | |
|---|---|---|---|
| hydrochloric acid | hypoiodous acid | oxalic acid | benzenesulfonic acid |
| hydrobromic acid | hypochlorous acid | tartaric acid | ethanesulfonic acid |
| sulfuric acid | hypobromous acid | p-toluenesulfonic acid | formic acid |
| nitric acid | perchloric acid | methanesulfonic acid | naphthalenesulfonic acid |
| phosphoric acid | peroxydisulfuric acid | fumaric acid | maleic acid |
| iodic acid | peroxydicarbonic acid | citric acid | amino acid |
| peroxycarbonic acid | pyrophosphoric acid | nicotinic acid | lactic acid |
| pyrosulfuric acid | pyrosulfurous acid | resin acid | acetic acid |
| tetrathioic acid | thiosulfuric acid | malic acid | ascorbic acid |
| chloric acid | metaphosphoric acid | benzoic acid | salicylic acid |
| hydroiodic acid | hydronitric acid | caffeic acid | sorbic acid |
| hydrofluoric acid | hydrogen sulfide | fumaric acid | ethanedioic acid |
| hydrochloric acid | tetraboric acid | succinic acid | pyruvic acid |
| carbonic acid | bromic acid | α-keto-succinic acid | trifluoroacetic acid |
| sulfurous acid | phosphorous acid | tetrasulfonic acid | |
| chlorous acid | nitrous acid | | |
| orthophosphoric acid | orthosulfuric acid | | |
| orthocarbonic acid | | | |

EXAMPLE 2

This example discloses a method for the preparation of dimethylamino glaucocalyxin A hydrochloride, which comprises mainly the following steps:

STEP ONE: The preparation of dimethylamino glaucocalyxin A.

1. Glaucocalyxin A (1.00 g) was mixed with an organic solvent (20 mL) under stirring at room temperature till the glaucocalyxin A was dissolved completely.

2. After filtration, dimethylamine solution (33%, 0.68 mL) was added drop-wise with stirring, and the mixed solution was stirred for 1~2 h at room temperature and monitored by TLC. 3. After completion of the reaction, the reaction system was subjected to distillation under reduced pressure at 40~50 dimethylamino glaucocalyxin A (1.05 g) as powder. The yield of dimethylamino glaucocalyxin A was 93%, and its purity was 99.2% by HPLC.

STEP TWO: The preparation of dimethylamino glaucocalyxin A hydrochloride.

1. To an organic solvent (10 mL) was added dimethylamino glaucocalyxin A (1.00 g) under ice bath, and the mixture was completely stirred till the dimethylamino glaucocalyxin A was dissolved.

2. After filtration, at a controlled temperature 0, hydrogen chloride solution was added to the mixture until pH 7 was reached, and the resultant was then stirred for 30 min to give a white solid.

3. The precipitation was filtered to afford dimethylamino glaucocalyxin A hydrochloride (1.00 g) as a white-like solid, with a yield of 92% and a purity of 99.5% by HPLC.

In practice, the organic solvents used in the STEP ONE and STEP TWO described above may be one or more of the following solvents: alcohol, ketone, ether, ester and haloalkane. In the present example, the organic solvent in STEP ONE is methanol, and the organic solvent in STEP TWO is isopropyl alcohol.

In other examples, the alcohols described above may be any one or more selected from the group consisting of methanol, ethanol, isopropanol, isobutanol and tert-butanol; the ketone described above is acetone or 2-butanone; the ether described above may be any one or more selected from the group consisting of ethyl ether, dioxane, isopropyl ether, methyl tert-butyl ether and tetrahydrofuran; the ester described above may be any one or more selected from the group consisting of methyl acetate, ethyl acetate and butyl acetate; the haloalkane described above is dichloromethane or trichloromethane.

The hydrogen chloride solution used in STEP TWO may be any one selected from the group consisting of aqueous solution of hydrogen chloride, methanol solution of hydrogen chloride, ethanol solution of hydrogen chloride, isopropanol solution of hydrogen chloride, n-propanol solution of hydrogen chloride, isobutanol solution of hydrogen chloride, ethyl acetate solution of hydrogen chloride, acetone solution of hydrogen chloride, ethyl ether solution of hydrogen chloride and dioxane solution of hydrogen chloride.

In the present example, the hydrogen chloride solution described above is, preferably, isopropanol solution of hydrogen chloride.

Figure 2:
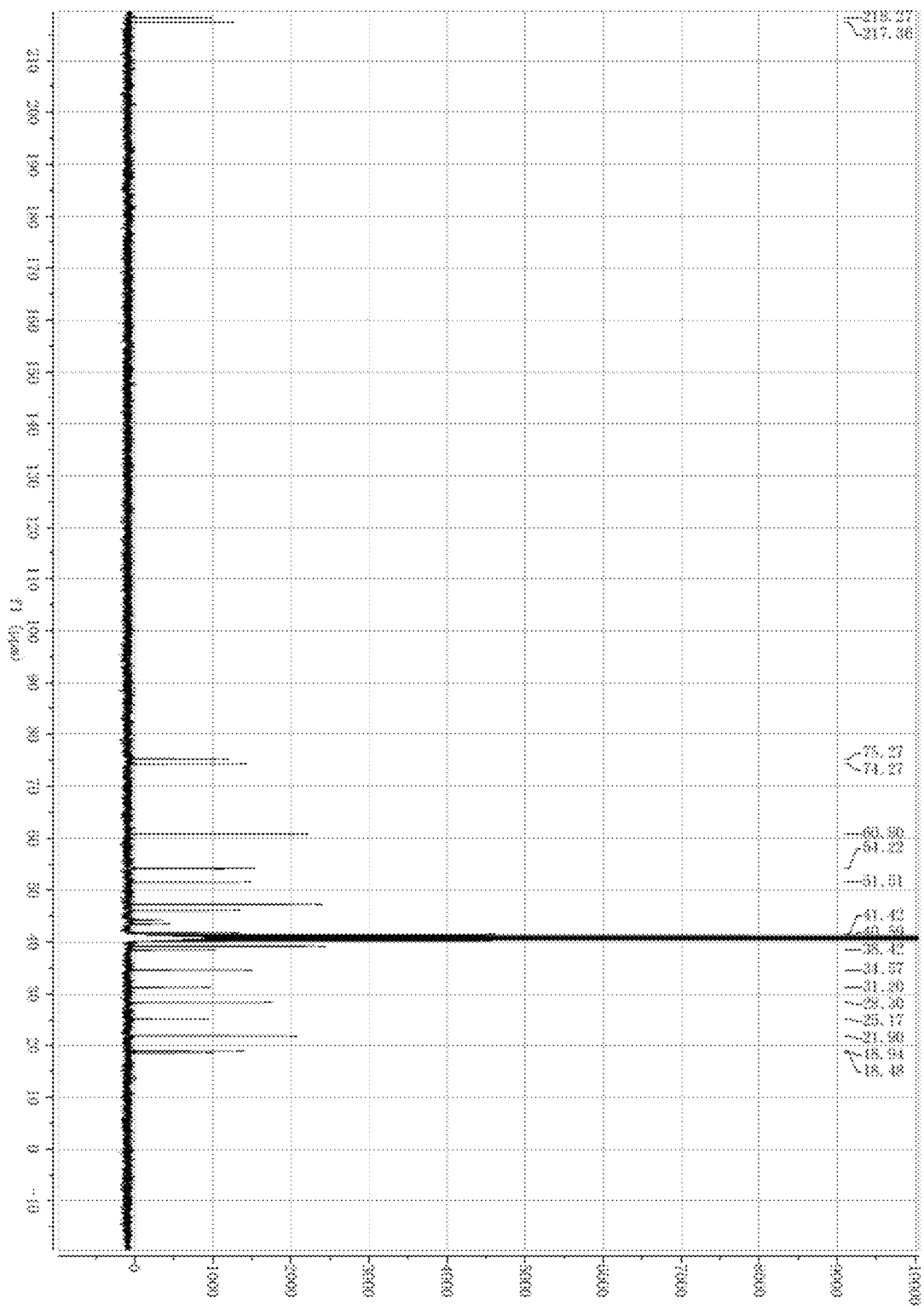
FIG. 2 shows a $^{13}$C NMR spectrum of a glaucocalyxin A derivative of the present invention.

In the present example, the dimethylamino glaucocalyxin A hydrochloride was characterized by H spectrum using NMR, and the result was shown as FIGS. 1-2.

As seen from FIG. 1, the molecular formula of dimethylamino glaucocalyxin A hydrochloride salt is $C_{22}H_{36}ClNO_4 \cdot HCl$, $^1H$ NMR(DMSO)δ:0.98(6H,d,2×CH$_3$), 1.05(3H, m, CH$_3$), 1.74(6H, m, 2×CH$_3$), 3.91(1H,s,C—H), 6.20(1H,s,C—H), 4.83(1H,s,C—H), 5.86(1H,s,C—H), 6.20(1H,s,C—H), 10.58(1H,s,O—H).

As seen from FIG. 2, the molecular formula of dimethylamino glaucocalyxin A hydrochloride salt is $C_{22}H_{36}ClNO_4 \cdot HCl$, $^{13}C$ NMR(DMSO)δ:

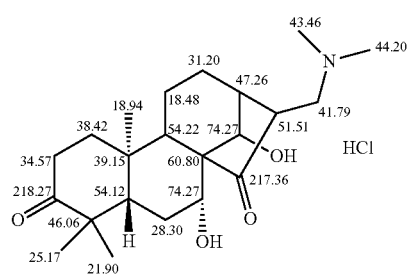 [SMILES: CN(C)CC1C(=O)C23C(O)C1CCC2[C@]1(C)CCC(=O)C(C)(C)[C@H]1C[C@H]3O ; Cl]

Figure 3:
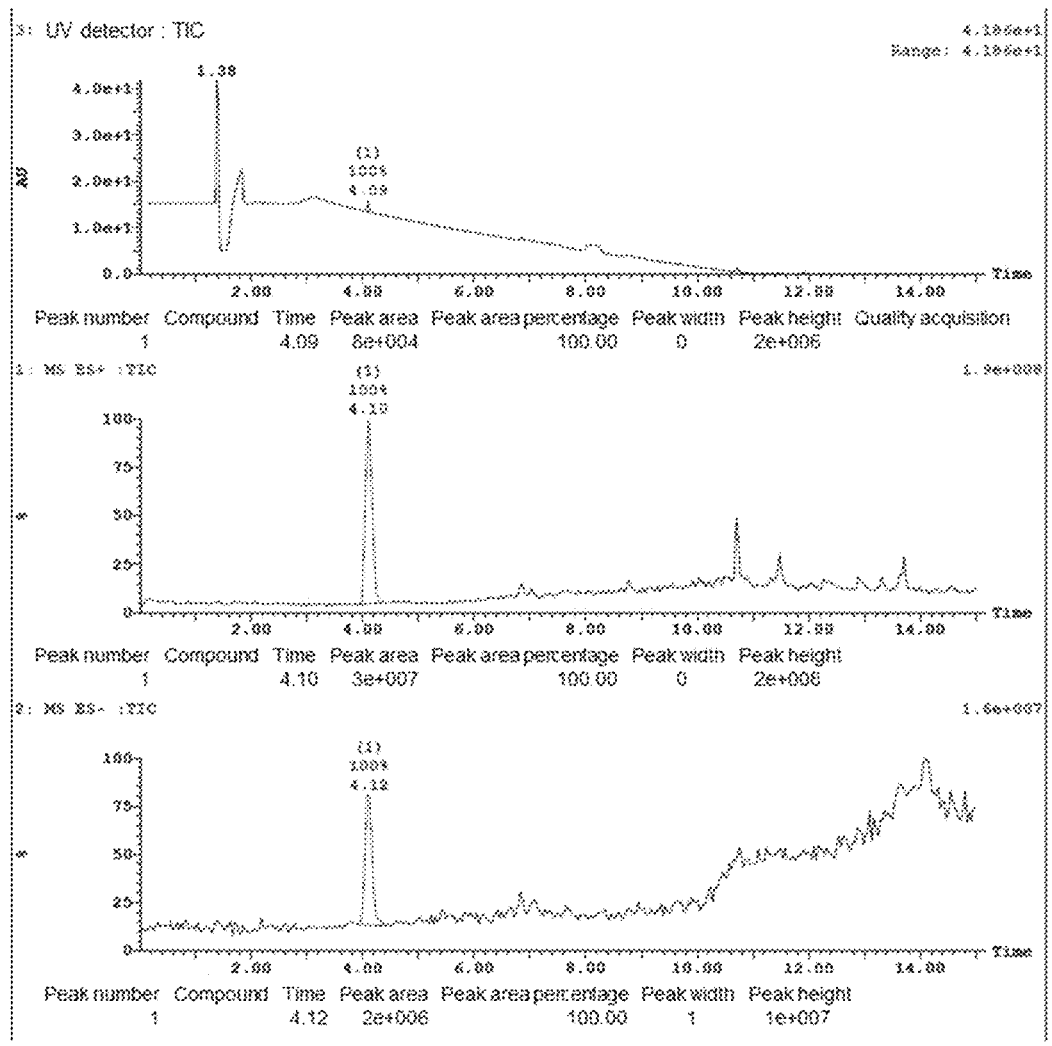
FIG. 3 shows a LC-MS spectrum of a salt of glaucocalyxin A derivative of the present invention.
Figure 3:
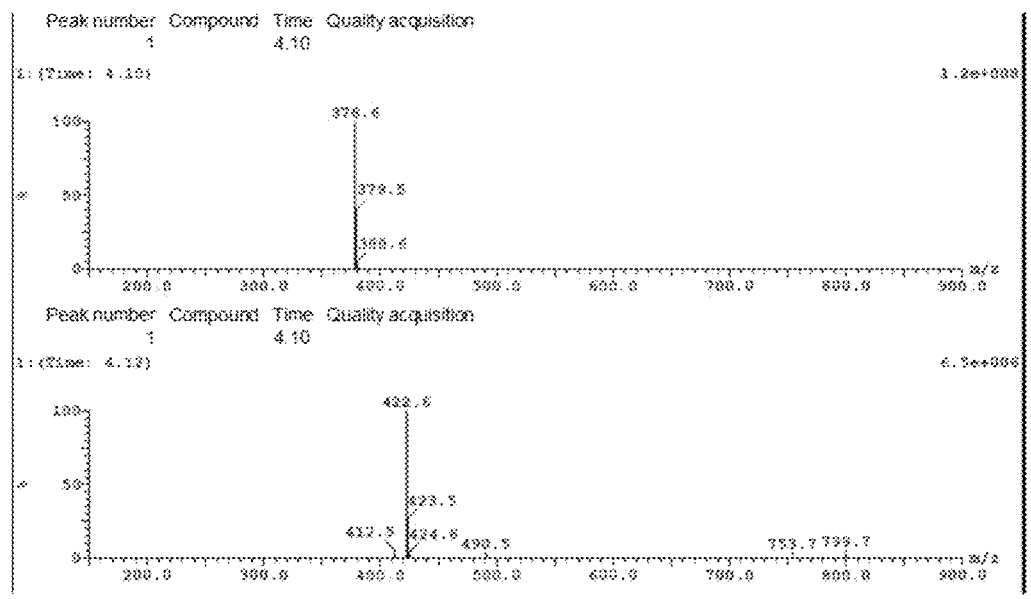

In the present example, the obtained dimethylamino glaucocalyxin A hydrochloride was subjected to LC-MS detection, and the detection result was shown as FIG. 3.

As seen from the spectrum of FIG. 3, the molecular formula of dimethylamino glaucocalyxin A hydrochloride salt is $C_{22}H_{36}ClNO_4 \cdot HCl$, MS m/e: 378.6 (M+).

EXAMPLE 3

The procedure of Example 3 was substantially identical to that of Example 2, except that the controlled temperature and pH in the preparation of dimethylamino glaucocalyxin A hydrochloride in STEP TWO were different. In the present example, the controlled temperature was −30

EXAMPLE 4

The procedure of Example 4 was substantially identical to that of Example 2, except that the controlled temperature and pH in the preparation of dimethylamino glaucocalyxin A hydrochloride in STEP TWO were different. In the present example, the controlled temperature was 60

EXAMPLE 5

Compared to Example 2, the procedure of Example 5 involves some differences in that the controlled temperature was −10 in the preparation of dimethylamino glaucocalyxin A hydrochloride in STEP TWO.

EXAMPLE 6

Compared to Example 2, the procedure of Example 6 involves some differences in that the controlled temperature was 20 in the preparation of dimethylamino glaucocalyxin A hydrochloride in STEP TWO.

The organic solvents used in Examples 2-6 described above are those enumerated in the embodiments. The hydrogen chloride solution is most preferably isopropanol solution of hydrogen chloride or ethanol solution of hydrogen chloride, the reaction temperature in the STEP TWO is most preferably in the range of −10~20 and the pH is most preferably 7.

As described in the Example below, the glaucocalyxin A derivative provided by the present invention was subjected to efficacy experiments. It can be known from the experiments that the glaucocalyxin A derivative can be used in the manufacture of a medicament against autoimmune diseases and cancers, such as triple-negative breast cancer, glioma, cervical cancer, esophageal cancer, lung cancer, liver cancer, choriocarcinoma, oral epidermoid carcinoma, prostate cancer, rectal cancer. Especially for the triple-negative breast cancer and glioma, the glaucocalyxin A derivative shows high targetability. The glaucocalyxin A derivative can be used in the medicament for the treatment of triple-negative breast cancer and fill the gaps in the treatment of triple-negative breast cancer. The autoimmune diseases comprise systemic lupus erythematosus or psoriasis.

EXAMPLE 7

Cell Proliferation Assay (MTT):

The experiment assaying the inhibition of dimethylamino glaucocalyxin A hydrochloride salt (hereinafter referred to as GH02) and glaucocalyxin A (i.e. GLA) on cell proliferation of cancer cell lines was performed as follows: cells of cancer cell lines were adjusted to a density of $10^4/100$ μL and were seeded into 96-well plates at 100 μL per well and cultured overnight until the cells were completely adherent and grown up to 70-80% confluence. The mother liquid of GH02 and GLA (both of which concentrations were 100 mM) were diluted with complete medium, respectively, to final concentrations of 1, 3.125, 6.25, 12.5, 25, 50, 100 μmol/L, and then such diluted solutions were added into wells of 96-well plates, with each concentration being performed in 4 replicates, and the group without cells acting as blank control, and then incubated in the incubator at 37₂. After incubation for 48 h, MTT was added to each well to a final concentration of 0.5 mg/ml and further incubated in the incubator at 37₂ for 4 h. Subsequently, the supernatant was removed, 150 μL DMSO was added to each well and incubated with shaking for 10 min, and then the absorbance was measured at 490 nm on a microplate reader.

Inhibitory rate of the cell proliferation=[(absorbance of the control group−absorbance of blank)− (absorbance of the medication group−absorbance of blank)]/(absorbance of the control group−absorbance of blank)%

Figure 4:
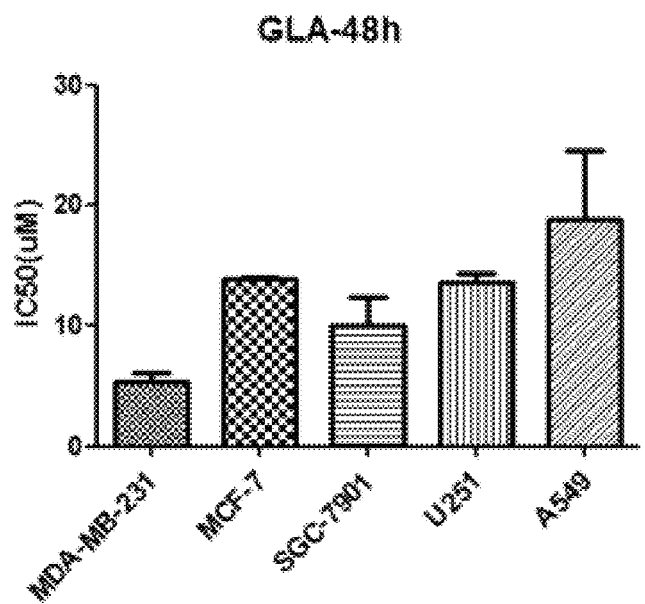
FIG. 4 shows a graph depicting IC$_{50}$ values (i.e., half effective inhibitory concentration) of a glaucocalyxin A derivative of the present invention for the inhibition of proliferation of five types of cell lines.
Figure 5:
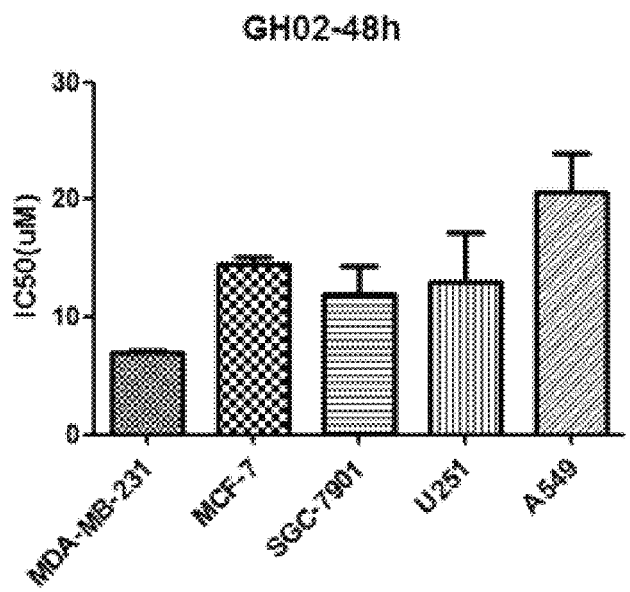
FIG. 5 shows a graph depicting IC$_{50}$ values of GLA for the inhibition of proliferation of five types of cell lines.
Figure 6:
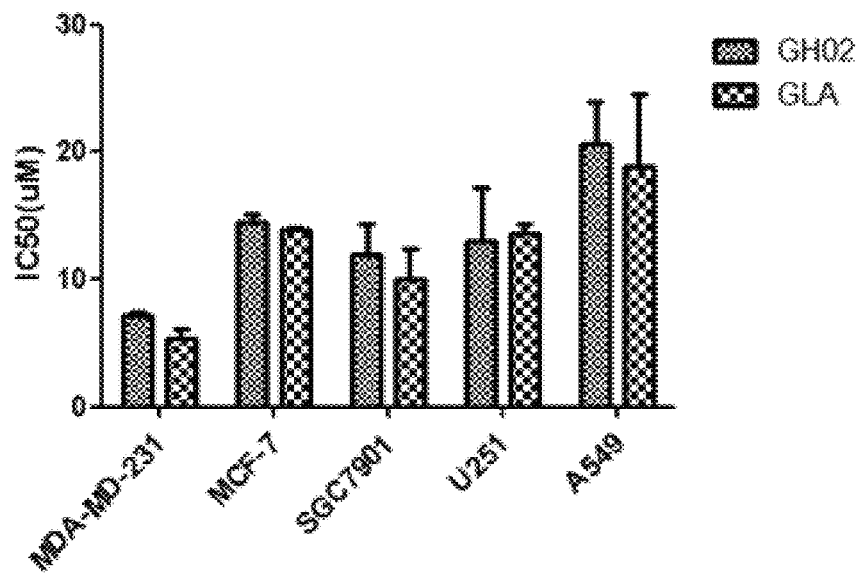
FIG. 6 shows the comparison of the IC$_{50}$ of a glaucocalyxin A derivative of the present invention for the inhibition of proliferation of various cell lines with that IC$_{50}$ of GLA.

As shown in FIG. 4 to FIG. 6, MDA-MB-231 and MCF-7 are cell lines of breast cancer, SGC-7901 is a cell line of gastric cancer, U251 is a cell line of glioma, and A549 is a cell line of lung cancer.

FIG. 4 shows the IC$_{50}$ values of GH02 against five cell lines described above, as seen from which, the GH02 displayed the lowest IC$_{50}$ value against the MDA-MB-231 breast cancer cell line, i.e. GH02 exhibited the best efficacy against breast cancer.

FIG. 5 shows the IC$_{50}$ values of GLA against five cell lines described above, as seen from which, the GLA displayed the lowest IC$_{50}$ value against the MDA-MB-231 breast cancer cell line; and as seen from which, in combination with FIG. 6, GH02 and GLA exhibited the best efficacy against breast cancer.

Figure 7:
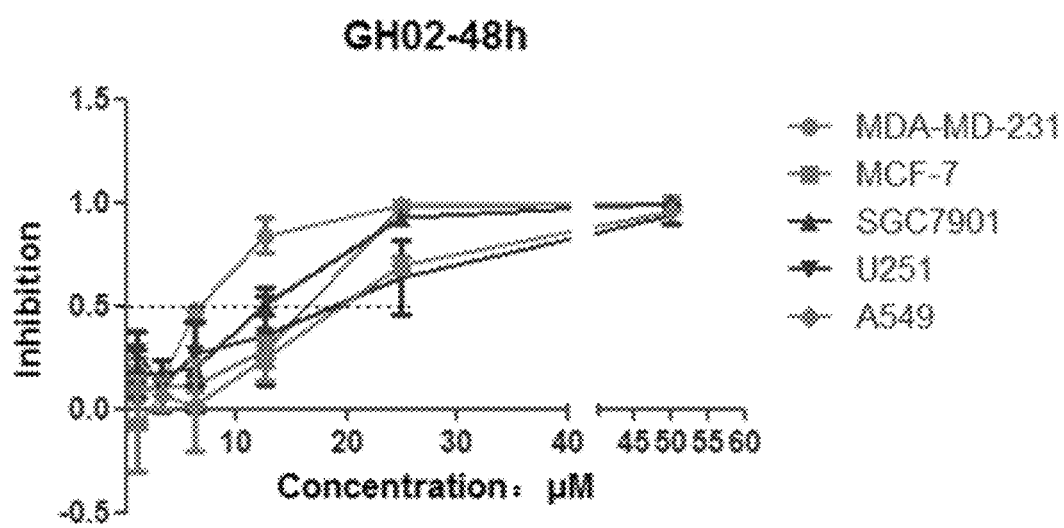
FIG. 7 shows a X-Y scatter plot of the concentration versus inhibitory rate of a glaucocalyxin A derivative of the present invention.

As shown in FIG. 7, the inhibition of GH02 on each of the five cell lines described above increased with the increase of the concentration of GH02, i.e. it can inhibit the proliferation of cancer cells.

Figure 8:
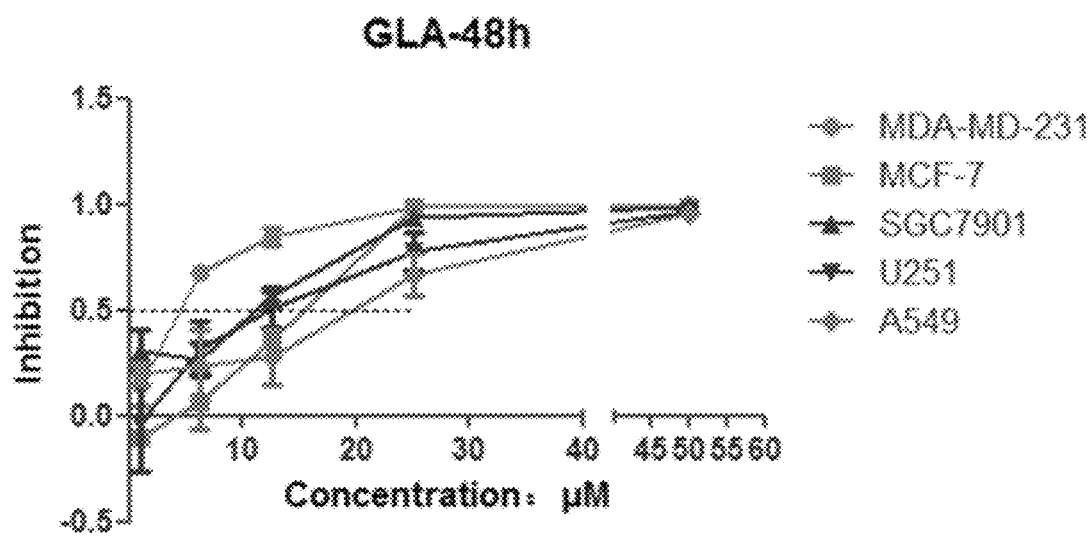
FIG. 8 shows a X-Y scatter plot of the concentration versus inhibitory rate of GLA.

As shown in FIG. 8, the inhibition of GLA on each of the five cell lines described above increased with the increase of the concentration of GLA, i.e. it can inhibit the proliferation of cancer cells.

In addition, it can be understood that, as shown in FIG. 7 and FIG. 8, GH02 and GLA displayed the lowest IC$_{50}$ values and the highest inhibitory rate against the MDA-MB-231 breast cancer cell line, and thus the glaucocalyxin A derivative of the present invention exhibited the best inhibition effect on breast cancer.

The foregoing description of the disclosed embodiments will enable one skilled in the art to achieve or use the present invention. Various modifications to these embodiments will be apparent to those skilled in the art, and the general principles defined herein may be embodied in other embodiments without departing from the spirit or scope of the invention. Accordingly, the invention is not to be limited to the embodiments shown herein, but is to be accorded the widest scope consistent with the principles and novel features disclosed herein.

The invention claimed is:

1. Glaucocalyxin A derivative represented by formula (I):

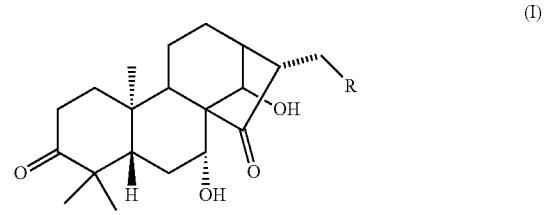

wherein R is any one selected from the group consisting of dimethylamino, diethylamino, piperidine-1-yl, piperazine-1-yl, hexamethyleneiminyl, morpholine-1-yl, N-phenyl-N-(3-oxocyclohexanyl)amino, N-p-chlorophenyl-N-(2-oxo-butanyl)amino, N-2-chlorophenyl-N-(2-oxo-butanyl)amino, benzylamino, purinyl-9-yl, 2-amino-6-hydroxypurine-9-yl, 4-methylpiperazine-1-yl, N-phenyl-N-methyl-amino, dibenzyl-amino, imidazole-1-yl, 2-methyl imidazole-1-yl, N-phenyl-N-(3-oxo-butanyl)amino, pyrrole-1-yl, 2-hydroxyacylpyrrole-1-yl, 2-methylpyrrolidine-1-yl, 3-methylpyrrole-1-yl, 2-oxo-pyrrole-1-yl, 3-aminoacylphenylamino, p-aminoacylphenylamino, amino acid substitutional;

or a salt thereof.

2. A method for preparation of glaucocalyxin A derivative according to claim 1, which comprises subjecting glaucocalyxin A and a R group donor compound to an addition reaction in the presence of a catalyst to afford the product.

3. The method according to claim 2, wherein the catalyst is any one or more selected from the group consisting of sodium methoxide, sodium ethoxide, pyridine, sodium carbonate and potassium carbonate.

4. The method according to claim 2, wherein the mole ratio of the R group to the glaucocalyxin A is (1 to 10): 1.

5. The method according to claim 2, wherein the mole ratio of the catalyst to the glaucocalyxin A is (1 to 10): 1.

6. The method according to claim 2, wherein the reaction is carried out at a temperature between −30° C. and 60° C.

7. The method according to claim 2, wherein the reaction is carried out in a solvent which comprises any one or more selected from the group consisting of alcohol, ketine, ether, ester and haloalkane.

8. The method according to claim 7, wherein the alcohol comprises any one or more selected from the group consisting of methanol, ethanol, isopropanol, isobutanol and tert-butanol; the ketone comprises any one or more selected from the group consisting of acetone and 2-butanone; the ether comprises any one or more selected from the group consisting of ethyl ether, dioxane, isopropyl ether, methyl tert-butyl ether and tetrahydrofuran; the ester comprises any one or more selected from the group consisting of methyl acetate, ethyl acetate and butyl acetate; the haloalkane comprises dichloromethane and trichloromethane.

9. The method according to claim 7, further comprising a step of evaporating the solvent and/or detecting with TLC and/or HPLC after the reaction.

10. A method for preparation of the salt of glaucocalyxin A derivative according to claim 1, comprising:
dissolving the glaucocalyxin A derivative into an organic solvent to form a solution, then subjecting the solution and an acid to a salt formation reaction, while controlling the pH of the solution, to give the salt of glaucocalyxin A derivative.

11. The method according to claim 10, wherein the acid includes organic acid and inorganic acid.

12. The method according to claim 11, wherein the inorganic acid comprises any one selected from the group consisting of hypoiodous acid, hypochlorous acid, hypobromous acid, iodic acid, perchloric acid, peroxydisulfuric acid, peroxydicarbonic acid, peroxycarbonic acid, pyrophosphoric acid, pyrosulfuric acid, pyrosulfurous acid, tetrathioic acid, phosphoric acid, thiosulfuric acid, sulfuric acid, chloric acid, metaphosphoric acid, hydroiodic acid, hydronitric acid, hydrofluoric acid, hydrogen sulfide, hydrochloric acid, hydrobromic acid, tetraboric acid, carbonic acid, nitric acid, bromic acid, sulfurous acid, phosphorous acid, chlorous acid, hydrochloric acid, nitrous acid, orthophosphoric acid, orthosulfuric acid and orthocarbonic acid; and the organic acid comprises any one selected from the group consisting of tartaric acid, oxalic acid, malic acid, citric acid, ascorbic acid, benzoic acid, salicylic acid, caffeic acid, lactic acid, sorbic acid, fumaric acid, formic acid, acetic acid, benzoic acid, ethanedioic acid, succinic acid, pyruvic acid, α-keto-succinic acid, benzenesulfonic acid, ethanesulfonic acid, resin acid, trifluoroacetic acid, maleic acid, tetrasulfonic acid, methanesulfonic acid, fumaric acid and amino acid.

13. The method according to claim 10, wherein the organic solvent comprises any one or more selected from the group consisting of alcohol, ketone, ether, ester and haloalkane.

14. The method according to claim 13, wherein the alcohol comprises any one or more selected from the group consisting of methanol, ethanol, isopropanol, isobutanol and tert-butanol; the ketone comprises any one or more selected from the group consisting of acetone and 2-butanone; the ether comprises any one or more selected from the group consisting of ethyl ether, dioxane, isopropyl ether, methyl tert-butyl ether and tetrahydrofuran; the ester comprises any one or more selected from the group consisting of methyl acetate, ethyl acetate and butyl acetate; the haloalkane comprises dichloromethane and trichloromethane.

15. The method according to claim 10, wherein the pH of the solution is controlled by hydrogen chloride solution.

16. The method according to claim 15 wherein the hydrogen chloride solution comprises any one selected from the group consisting of aqueous solution of hydrogen chloride, methanol solution of hydrogen chloride, ethanol solution of hydrogen chloride, isopropanol solution of hydrogen chloride, n-propanol solution of hydrogen chloride, isobutanol solution of hydrogen chloride, ethyl acetate solution of hydrogen chloride, acetone solution of hydrogen chloride, ethyl ether solution of hydrogen chloride and dioxane solution of hydrogen chloride.

17. The method according to claim 15, wherein the pH of the solution is controlled between 6.0 and 8.0.

18. The method according to claim 10, wherein the reaction is carried out at a temperature between −30° C. and 60° C.

19. A method for treating a cancer selected from triple-negative breast cancer, glioma and lung cancer in a subject in need thereof, comprising administration of a medicament comprising dimethylamino glaucocalyxin A derivative or the salt thereof to the subject.

* * * * *